(12) United States Patent
Blumenkranz et al.

(10) Patent No.: US 9,005,099 B2
(45) Date of Patent: Apr. 14, 2015

(54) METHOD AND APPARATUS FOR THE DELIVERY OF PHOTOCHEMICAL (CROSS-LINKING) TREATMENT TO SCLERAL TISSUE

(75) Inventors: Mark S. Blumenkranz, Portola Valley, CA (US); Edward E. Manche, Los Altos, CA (US); Satish V. Herekar, Palo Alto, CA (US); Donald J. Eaton, Los Altos, CA (US)

(73) Assignee: Seros Medical, LLC, Palo Alto, CA (US)

( * ) Notice: Subject to any disclaimer, the term of this patent is extended or adjusted under 35 U.S.C. 154(b) by 296 days.

(21) Appl. No.: 13/396,454

(22) Filed: Feb. 14, 2012

(65) Prior Publication Data

US 2012/0209051 A1  Aug. 16, 2012

Related U.S. Application Data

(60) Provisional application No. 61/443,191, filed on Feb. 15, 2011.

(51) Int. Cl.
  *A61M 37/00*  (2006.01)
  *A61F 9/00*  (2006.01)
  *A61F 9/007*  (2006.01)
  (Continued)

(52) U.S. Cl.
  CPC .............. *A61F 9/0017* (2013.01); *A61F 9/0079* (2013.01); *A61K 31/525* (2013.01); *A61K 41/0038* (2013.01); *A61N 5/062* (2013.01)

(58) Field of Classification Search
  CPC ........... A61N 5/062; A61N 2005/0661; A61N 5/0613
  USPC .............................................. 600/2; 606/4–6
  See application file for complete search history.

(56) References Cited

U.S. PATENT DOCUMENTS 5,133,708 A  7/1992  Smith
5,156,852 A *  10/1992  La Haye et al. ................ 424/617
(Continued)

FOREIGN PATENT DOCUMENTS

AU  2004200303  2/2004
AU  2007202052  5/2007
(Continued)

OTHER PUBLICATIONS

Wollensak, Gregor and Iomdina, Elena. Long-term Biomechanical Properties of Rabbit Sclera after Collagen Crosslinking Using Riboflavin and Ultraviolet A. Acta Ophtahlmologica 2009: 87: 193-98.*
(Continued)

*Primary Examiner* — Christine H Matthews
*Assistant Examiner* — Joshua D Lannu
(74) *Attorney, Agent, or Firm* — Squire Patton Boggs (US) LLP

(57) ABSTRACT

Delivery systems and methods for delivering riboflavin (R/F) and UVA irradiation to the sclera are disclosed. The R/F is delivered and then activated with UVA irradiation through the use of LEDs or optical fibers, thereby causing cross-linking of the collagen tissue. Delivery systems include implantable structures which provide surfaces that conform to the sclera. The delivery systems include various types of structures for delivery of R/F onto the sclera surface. Additionally, the delivery systems include UVA sources which provide irradiation of R/F in sclera collagen tissue.

6 Claims, 7 Drawing Sheets

(51) Int. Cl.
*A61K 31/525* (2006.01)
*A61K 41/00* (2006.01)
*A61N 5/06* (2006.01)

(56) References Cited

U.S. PATENT DOCUMENTS

| | | | |
|---|---|---|---|
| 5,643,299 | A | 7/1997 | Bair |
| 6,334,856 | B1 | 1/2002 | Allen et al. |
| 6,503,231 | B1 | 1/2003 | Prausnitz et al. |
| 6,611,707 | B1 | 8/2003 | Prausnitz et al. |
| 6,743,211 | B1 | 6/2004 | Prausnitz et al. |
| 7,226,439 | B2 | 6/2007 | Prausnitz et al. |
| 7,344,499 | B1 | 3/2008 | Prausnitz et al. |
| 7,918,814 | B2 | 4/2011 | Prausnitz et al. |
| 8,197,435 | B2 | 6/2012 | Prausnitz et al. |
| 8,257,324 | B2 | 9/2012 | Prausnitz et al. |
| 2002/0082543 | A1 | 6/2002 | Park et al. |
| 2005/0137531 | A1 | 6/2005 | Prausnitz et al. |
| 2005/0271590 | A1* | 12/2005 | Schwartz et al. ............ 424/9.5 |
| 2007/0142828 | A1 | 6/2007 | Peyman |
| 2007/0160592 | A1* | 7/2007 | Chornenky et al. .......... 424/94.6 |
| 2007/0260201 | A1 | 11/2007 | Prausnitz et al. |
| 2008/0015660 | A1* | 1/2008 | Herekar ........................ 607/88 |
| 2008/0183159 | A1 | 7/2008 | Preuss et al. |
| 2009/0182306 | A1 | 7/2009 | Lee et al. |
| 2009/0182373 | A1 | 7/2009 | Garcia et al. |
| 2009/0192437 | A1 | 7/2009 | Soltz |
| 2010/0057060 | A1 | 3/2010 | Herekar |
| 2010/0189817 | A1 | 7/2010 | Krueger et al. |
| 2010/0312191 | A1 | 12/2010 | Allen et al. |

FOREIGN PATENT DOCUMENTS

| | | |
|---|---|---|
| CA | 2330207 | 12/1999 |
| CA | 2510389 | 12/1999 |
| CA | 2376128 | 12/2000 |
| WO | WO 2007/131050 | 11/2007 |
| WO | WO 2009/094394 | 7/2009 |

OTHER PUBLICATIONS

International Search Report for PCT/US2012/025275, mailed Aug. 17, 2012, 12 pgs.

International Search Report for PCT/US2012/025039, mailed Aug. 17, 2012, 12 pgs.

Bruskov et al., "Heat-induced formation of reactive oxygen species and 8-oxoguanine, a biomarker of damage to DNA", Nucleic Acids Research vol. 30, No. 6, pp. 1354-1363 (2002).

Collin et al., "Online H/D exchange liquid chromatography as a support for the mass spectrometric identification of the oxidations products of melatonin", J. Mass. Spectrom. 44, pp. 318-329 (2009).

Ertan "Corneal Crosslinking for Different Corneal Diseases", Cataract & Refractive Surgery Today Europe pp. 25-28 (2009).

Grant et al., "Mechanical Investigations on Agar Gels Using Atomic Force Microscopy: Effect of Deuteration", Macromol. Mater. Eng. 297, pp. 214-218 (2012).

Iseli et al., "Efficacy and Safety of Blue-light Scleral Cross-linking", J. of Refractive Surgery vol. 24, pp. S752-S755 (2008).

Jiménez—Oxygen Photosensitization by EGFP and its Chromophore HBDI, Biophysical J. vol. 94, pp. 168-172 (2008).

Ma et al., "Generation of Singlet Oxygen via the Composites of Water-Soluble Thiol-Capped CdTe Quantum Dots-Sulfonated Aluminum Phthalocyanines", J. of Physical Chemistry B Letters 12, pp. 4465-4469 (2008).

Wollensak et al., "Collagen crosslinking of human and porcine sclera", J. Cataract Refract. Surg. 30, pp. 689-695 (2004).

Wollensak et al., "Long-term biomechanical properties of rabbit sclera after collagen crosslinking using riboflavin and ultraviolet A (UVA)", Acta Ophthalmol. 87, pp. 193-198 (2009).

Zhao et al., "Photoirradiation of dehydropyrrolizidine alkaloids—Formation of reactive oxygen species and induction of lipid peroxidation", Toxicology Letters 205, pp. 302-309 (2011).

Zhao et al., "Photoirradiation of polycyclic aromatic hydrocarbon diones by UVA light leading to lipid peroxidation", Chemosphere 85, pp. 83-91 (2011).

\* cited by examiner

METHOD AND APPARATUS FOR THE DELIVERY OF PHOTOCHEMICAL (CROSS-LINKING) TREATMENT TO SCLERAL TISSUE

This application claims the benefit of U.S. Provisional Patent Application No. 61/443,191 filed on Feb. 15, 2011 and is incorporated by reference herein.

BACKGROUND OF THE INVENTION

This invention is directed to designs and methods for delivering and infusing dosage forms containing riboflavin or photosensitizer analogues, or other ophthalmic formulations, into ocular tissue (such as equatorial and posterior sclera tissue). The riboflavin is then activated by delivering UVA irradiation onto the tissue which facilitates effective rigidity by cross-linking of collagen molecules therein.

Collagen cross-linking (CXL) in the cornea is now a widespread method used to stiffen and stabilize corneal tissue for the treatment of keratoconus, a degenerative collagenous disease. CXL has been shown to prevent the progression of keratonconus by collagen stiffening. There are other conditions and diseases of the cornea where CXL treatment has been shown to be safe and effective, for example: corneal ectasia, corneal ulceration, infective keratitis, and bullous keratopathy. Importantly, recent animal studies have shown that CXL has the same stabilizing effect on degenerative sclera tissue as it does on corneal tissue.

Progressive myopia primarily manifests in the pre-teen years due to unknown causes. The primary characteristics of this condition include the elongation of both eyes (i.e. the axial length of each eyeball progressively extends beyond 24 mm to over 26 mm) and greater than –6 diopters of ametropia. The stretching of the eye occurs over a period of years, usually beginning in early childhood (3 years old) and continuing until adulthood (18 years old). This stretching is accompanied by regional thinning of the sclera, primarily in the equator and posterior regions.

FIG. 1 compares a normal eye to a progressive myopic eye. The sclera covers the eyeball, except for the cornea, and the sclera's dense collagen fiber controls the size of the eye. As shown in FIG. 1, with a progressive myopic eye the scleral tissue has become stretched and thereby creates a mismatch between the eye's normal focal point and the axial length of the eye. A person with this condition becomes severely nearsighted (>–6 diopters).

Reduced visual acuities are not the only problem caused by progressive myopia. Additionally, there is an extremely high correlation (>75%) between the following serious conditions and unabated progressive myopia, which at a later age (usually >50 yrs) can induce pathologic sequelae (sometimes referred to as pathologic myopia), such as:

Retinal detachment
Choroidal Neo-Vascularization (CNV)
Lacquer cracks
Posterior staphylomas.

Currently there is no effective treatment for progressive myopia.

The invention herein described includes methodology for cross-linking scleral tissue. Cross-linking as discussed herein is a two-step process wherein tissue rigidity and shape stability are enhanced. The first step involves the application of a photo-sensitizer such as riboflavin (Vitamin B-2), which is infused into the collagen tissue of the sclera. There are several novel methods described herein for this infusion of the photo-sensitizer such as riboflavin (herein "R/F"). After the riboflavin saturates the scleral tissue, step two is ready to be implemented. This second step involves the generation of radical oxygen species through the application of ultraviolet light (herein "UVA") to the infused R/F in the scleral collagen tissue. Without being limited by theory, these radical oxygen species trigger the formation of covalent bonds between and within collagen strands as well as, it is hypothesized, bridging bonds between collagen fibrils and the local extracellular matrix (ECM). The result of this bonding is to impart an increase in biomechanical rigidity or stiffness to the treated ocular tissue.

Methods and apparatus to reduce, limit, and/or arrest progressive myopia through the application of novel cross-linking techniques is being proposed herein. As mentioned above, cross-linking of corneal tissue has become a standard of care in the EU, primarily for the treatment of keratoconus. However, there is a need to provide safe, rapid, and effective devices and techniques for cross-linking scleral collagen tissue with an outcome that affords patient comfort, stability, reliable uniformity and retention. Wollensak, Spoerl and Iseli are among the few researchers who have published their investigations of scleral crosslinking on enucleated porcine and in vivo rabbit eyes. Their results are promising and with only minor complications reported. However, the devices used in these studies are more suited for animal work and would not be adequate in a clinical setting. There is a need for more advanced devices which are suitable in both ophthalmological adult and pediatric surgical theaters.

SUMMARY OF THE INVENTIONS

Various embodiments of the present invention includes a method of treating ocular tissue comprising: providing an apparatus for delivering a drug formulation comprising riboflavin to scleral ocular tissue of a sclera; inserting the apparatus through an opening in a conjunctiva to deliver the drug formulation to targeted regions of the scleral ocular tissue; and allowing the drug formulation to diffuse from the apparatus into the targeted regions of the scleral tissue to soak the scleral tissue, wherein the drug formulation comprises riboflavin which is capable of being activated by UVA radiation for purposes of inducing cross-linking of scleral collagen tissue.

Various embodiments of the present invention includes a method of treating ocular tissue comprising: providing a mat containing a sponge comprising a source of riboflavin; disposing the mat through an opening in the conjunctiva; and soaking targeted regions of scleral tissue with riboflavin from the source through application of the sponge on the scleral tissue.

Various embodiments of the present invention includes a method of treating ocular tissue comprising: providing a mat comprising a source of UVA irradiation; disposing the mat through an opening in the conjunctiva; and irradiating targeted regions of scleral tissue with UVA radiation from the UVA source.

Various embodiments of the present invention include a system for treatment of the equatorial region of the sclera comprising: a cylindrical belt-like apparatus having an outer convex surface and an inner convex surface, wherein the apparatus is shaped so that the inner concave surface conforms to an equatorial region of a sclera of an eye when disposed around the equatorial region; channels within the apparatus for transporting and delivering R/F fluid to the sclera surface of the equatorial region of the sclera of an eye or no channels for transporting R/F fluid within the apparatus; and UVA sources embedded in the inner concave surface of the section for delivering UVA irradiation to the to the sclera surface of the equatorial region of the sclera of an eye exposed to R/F fluid.

Various embodiments of the present invention include a sponge mat system for delivery of R/F to the equatorial region of the sclera, wherein the sponge mat is placed circumferentially onto the sclera and under the four rectus muscles of the sclera; and, R/F is injected into the sponge mat through embeddded tubing with graduated holes that allow the R/F to be evenly distributed onto the sclera surface.

Various embodiments of the present invention include a system for treatment of the posterior region of the sclera comprising: an R/F applicator comprising a R/F sponge-mat having a concave porous surface for absorbing and delivering R/F fluid to a surface of the posterior segment of the sclera, wherein the R/F mat is sized to be inserted to the posterior segment of the sclera, wherein the concave surface is shaped to conform to a surface of the posterior segment of the sclera; and a UVA applicator comprising UVA mat having a concave surface including UVA sources attached or embedded in the concave surface of the U/VA mat for delivering UVA irradiation to a surface of the posterior segment of the sclera upon removal of the R/F applicator, wherein the UVA applicator is sized to be inserted onto the posterior segment of the sclera, wherein the concave surface is shaped to conform to a surface of the posterior segment of the sclera.

Various embodiments of the present invention include a system for treatment of the anterior region of the sclera comprising: an annular R/F applicator comprising an inner circular surface around a hole, an outer circular surface, a top surface, and a bottom surface, wherein the bottom surface has an inward radial curvature so that bottom surface conforms to the surface of an anterior region of the sclera when the annular R/F applicator is placed on the anterior region, wherein the hole allows the R/F applicator to avoid contact with the cornea, wherein channels embedded in the applicator allow delivery of R/F fluid to the anterior segment of the sclera when the R/F applicator is placed on the anterior segment of sclera; and an annular UVA applicator comprising an inner circular surface around a hole, an outer circular surface, a top surface, and a bottom surface, wherein the bottom surface has an inward radial curvature so that bottom surface conforms to the surface of an anterior region of the sclera when the annular R/F applicator is placed on the anterior region, wherein the hole allows the UVA applicator to avoid contact with the cornea, wherein UVA sources are attached or embedded in the bottom surface of the UVA applicator for delivering of UVA irradiation to a surface of the anterior segment of the sclera upon removal of the R/F applicator.

BRIEF DESCRIPTION OF THE DRAWINGS

The inventions herein have other advantages and features which will be more readily apparent from the following detailed descriptions and the appended claims, when taken in conjunction with the accompanying drawings, in which:

DETAILED DESCRIPTIONS OF THE INVENTIONS

The present inventions include embodiments of delivery systems and methods for delivering R/F and UVA to the sclera. The R/F is delivered and then activated (i.e., photonically energized for ROS generation) with UVA radiation thereby causing crosslinking of the collagen tissue. The R/F can be delivered through direct contact of an implantable structure having an open channel in contact with the sclera, a single sided sponge mat, or a dissolvable film. All of the foregoing deliver the R/F into the scleral tissue by a soaking process. A sponge refers to a material that is porous and is capable of absorbing, retaining, and releasing a fluid.

The type of devices for delivering the R/F described herein can be inserted following a peritomy, thereby enabling direct contact with the scleral tissue. The types of direct contact, as described herein, allow soaking or infusing of the R/F into the sclera. In a peritomy, a surgical incision of the conjunctiva and sub-conjunctival tissue is performed partially or wholly at the corneo-scleral boundary to expose the sclera.

After R/F is sufficiently soaked into the sclera, the invention herein includes several methods whereby the scleral tissue is irradiated with UVA. The source of the UVA illumination can be LEDs or can be fiber coupling to a UVA source. Both of these methods permit high intensity, uniform scleral UVA irradiation. The type of devices used to accomplish this type of UVA delivery include a mat that can sit directly or indirectly on the scleral tissue, wherein the latter case there may be an interface between the mat and the tissue.

Delivery of R/F onto the sclera can be done: (a) in the equatorial region of the sclera beneath the rectus muscles; (b) in the four quadrants between the rectus muscles; (c) around the peripapillary region of the posterior sclera; and, (d) onto the anterior segment of the sclera. Likewise, the UVA irradiation can be delivered onto these same four areas.

The R/F delivery may be accomplished with a structure, such as a mat, that can be inserted under the conjunctiva, and which may contain or include tubing for irrigation and aspiration, and a channel as part of the mat which enables delivery of R/F directly to the sclera. This type of mat is referred to above in FIGS. 2-5 as an Equatorial Sclera-Mat System. Although "mat" is used herein to refer to devices including a mat, a "mat" generally refers to a broad, flat structure with a thickness much smaller than the dimensions characterizing its flat surface. A mat may further provide for optimal flexibility for insertion and extraction.

Figure 10:
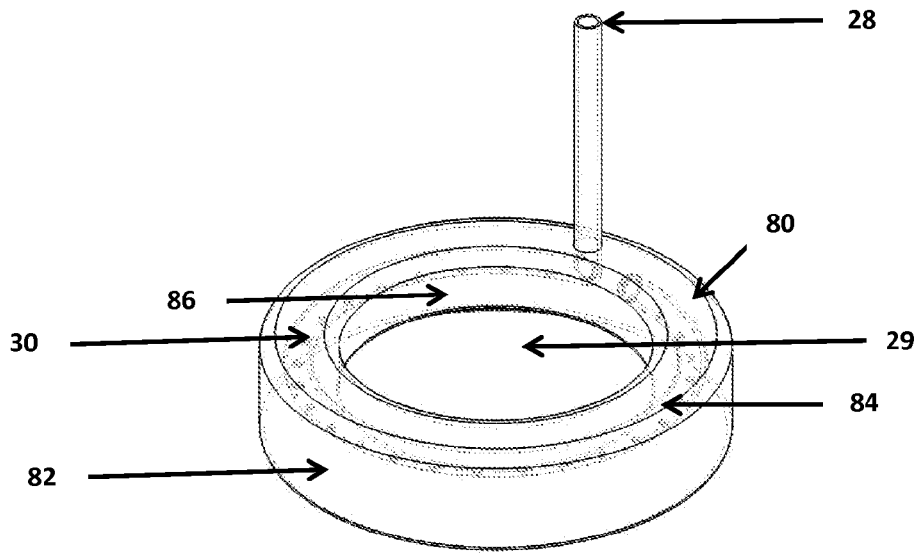
FIG. 10 depicts an anterior R/F Sponge-Mat delivery system for the anterior sclera.

Upon completion of a peritomy, for purposes of initiating the cross-linking procedure (R/F soaking plus UVA irradiation) in the equatorial region of the sclera, the Equatorial Sclera-Mat System (FIGS. 2-5), or the equatorial Sponge- Mat (FIG. 6), as the case may be, may be inserted onto the scleral tissue in the equatorial region to provide R/F delivery. In addition to, or commensurate with, the foregoing R/F delivery, a posterior Sponge-Mat for R/F delivery (FIG. 7) may be inserted into the posterior area of the sclera. In general, Cross-linking in the anterior region of the sclera may be done following either a complete or partial peritomy. Delivery of R/F to the anterior region of the sclera is performed with the application of an embodiment that includes a soaking process using a donut-shaped anterior R/F Sponge-Mat (FIG. 10). The use of a single sided scleral sponge for R/F delivery, as described in the foregoing applications, will provide adequate dwell time with lower viscosity R/F formulations (dextran-free), and which formulations are designed for high diffusivity. R/F will be delivered to the Equatorial Sclera-Mat, equatorial Sponge-Mat, posterior Sponge-Mat and anterior Sponge-Mat after their respective insertions. As an alternative, R/F may be delivered through the insertion of a dissolvable R/F polymer film patch that is shape-matched to be inserted onto the bottom of the Equatorial Sclera-Mat. Through the use of these various foregoing embodiments, a continuous or near continuous soaking of R/F into the scleral tissue is provided until the R/F has thoroughly saturated the targeted areas to a depth of about 300 um from the surface of the sclera. The amount of time required for adequate soaking of R/F into the scleral tissue may be about 10 minutes or less, or about 10-15 minutes, or longer than 15 minutes. Following the R/F delivery, it is preferable and may be necessary to irrigate and aspirate R/F tear film from the scleral surface in order to prevent this film from inhibiting effective delivery of UVA.

The R/F formulation used may contain R/F (concentration ranging from at or about 0.1%-1.0%) combined with deuterated water (D2O)—up to or about 99.9%+ concentration). R/F formulations as disclosed in PCT/US2010/045356, which is incorporated herein by reference, may also be used. UVA may be delivered into the scleral tissue through fractionation and pulsation techniques and protocols as disclosed in PCT/US2011/034823 and U.S. patent application Ser. No.: 13/068,126, which is incorporated by reference herein, thereby maximizing the use (i.e., ROS conversion efficiency) of dissolved oxygen in the ocular tissue. The present invention includes the use of the R/F formulation containing D2O, which enables the use of a shorter time period to cross-link collagen fibers, and at the same time, creates higher cross-link densities than can be achieved with prior art treatments Support for such use of $D_2O$ is supported by the following references:

(1) Photoirradiation of dehydropyrrolizidine alkaloids—formation of reactive oxygen species and induction of lipid peroxidation. Zhao Y, Xia Q, Yin J J, Lin G, Fu P P. Toxicol Lett. 2011 Sep. 10; 205(3):302-9.

(2) Photoirradiation of polycyclic aromatic hydrocarbon diones by UVA light leading to lipid peroxidation. Zhao Y, Xia Q, Yin J J, Yu H, Fu P P. Chemosphere. 2011 September; 85(1):83-91.

(3) Mechanical effects on Agar gels using Atomic Force Microscopy: Effect of Deuteration. Grant C, Twigg P, Savage M, Greig D. Macromol. Mater. Eng. 2011 295, 000-000

(4) Heat induced formation of ROS, and 8-oxoguanine, a DNA biomarker. Bruskov V, Malakhova L, Masalimov Z, Chernikov A. Nucleic Acids Research. 2002 Vol 30, No 6.

Figure 11:
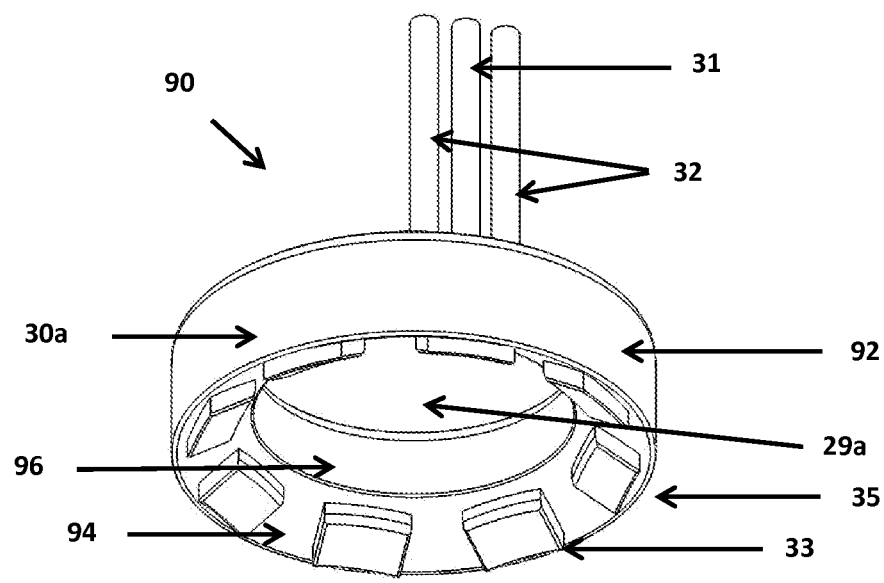
FIG. 11 depicts an anterior UVA-Mat for irradiation delivery to the anterior sclera.

Following delivery of R/F into the scleral tissue by one of the embodiments hereinabove described, the second step to the cross-linking process involves delivery of UVA irradiation. This is done with the Equatorial Sclera-Mat (FIGS. 2-5), the posterior UVA-Mat (FIG. 8), and the anterior UVA-Mat (FIG. 11). These UVA delivery mats may have the following irradiation components: 1) UVA LEDs; 2) optical fiber arrays; 3) one piece molded plastic light guides; or 4) light extracting and diffusing elements. With all four of these components the UVA may be delivered in a single side emitting aperture. These mat configurations may also possess adequate mechanical flexibility and have low profiles for ease of placement and positioning on the scleral tissue. Following delivery of irradiation to the scleral tissue, the UVA delivery mats are removed from the eye.

When optical fibers are used in the invention, these have the capability of delivering UVA onto ocular tissue, and, at the same time, transmitting light back from the ocular tissue. This light from the ocular tissue (which is generated by R/F fluorescence) can be transmitted back to the mat in order to sample these wavelengths. The purpose of sampling such wavelengths is to determine the concentration and viability (i.e., degree of photo bleaching) of R/F in the ocular tissue and thereby confirm the presence of a therapeutic dose of active riboflavin, or the need for additional riboflavin instillation, in the ocular tissue.

The present invention generally relates to various methods and apparatuses to dose ocular tissue with photo-chemical exposures. Specifically, this may involve drug transfusion, such as riboflavin formulations, into the sclera. Additionally, these methods provide for photonic (typically UVA) delivery to the sclera after transfusion.

As used herein, the words "light" and "optical" include not only the visible spectrum but also infrared and near UV spectrum. The term "light" includes coherent and incoherent as well as monochromatic polychromatic or multispectral light.

The invention herein includes UVA LEDs which provide for targeted illumination delivered to scleral tissue at wavelengths suitable for photosensitizer activation. Various manufacturers, such as Nichia Corp. (Japan) provide a variety of LED configurations. The product described herein incorporates specific sizes of LEDs that will generate patterns which enable the geometrical configuration of LEDs so selected to provide an irradiance which is effective for optimal cross-linking in situ. For example, the inventions herein provide for the following attributes: (1) a range of irradiances from 3 mW/cm2 to 100 mW/cm2 which are available in the 365 nm-375 nm wavelength, which is the UVA range of choice; (2) a depth modulation for cross-linking that can range from about 0.1 mm thickness to 1.0 mm, and this depth modulation (which is the depth to which cross-linking occurs) is enabled due to dynamically adjustable R/F concentrations and UVA irradiances; and, (3) a spatially uniform UVA delivery in the range of about 50 to 90 percent. In addition to the foregoing attributes, the inventions herein described also provide for the ability to control temperature in the scleral tissue wherein such temperature does not exceed 42 degrees C. This temperature control is necessary because the LEDs generate substantial heat. However, they are actively cooled with saline solution, which is circulated over a copper-backed printed circuit board (PCB), and thereby extracts heat that is generated by the LEDs.

Although the detailed descriptions of the inventions herein contain many specifics, these should not be construed as limiting the scope of the inventions but merely as illustrating different examples and aspects of the inventions. It should be appreciated that the scope of the inventions includes other embodiments not discussed in detail below. Various other modifications, changes and variations which will be apparent to those skilled in the art may be made in the arrangement, operation and details of the method and apparatus of the present inventions disclosed herein without departing from the spirit and scope of the inventions as described here.

Figure 1:
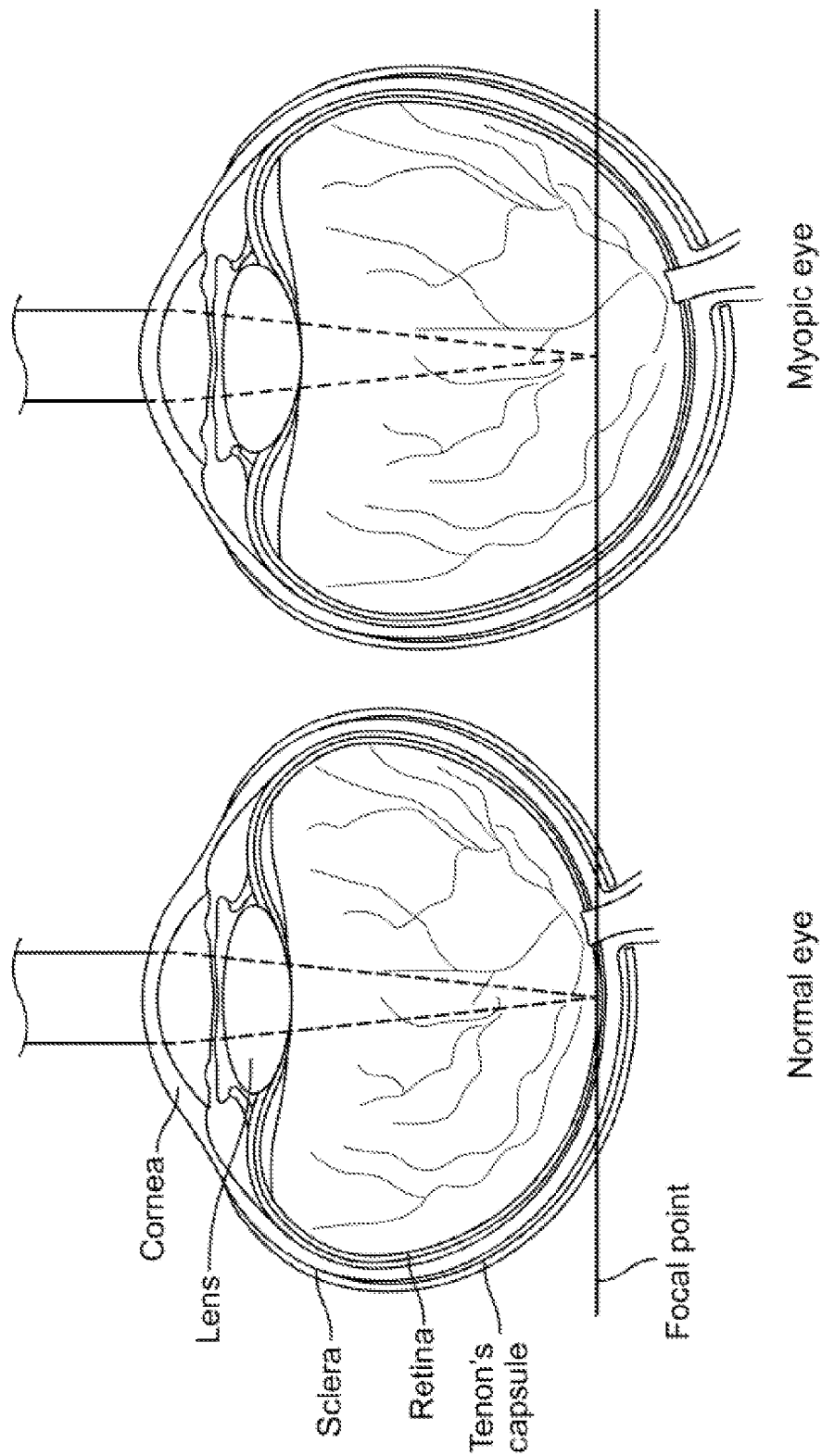
FIG. 1 depicts the comparison of a normal eye to a progressive myopic eye.
Figure 2:
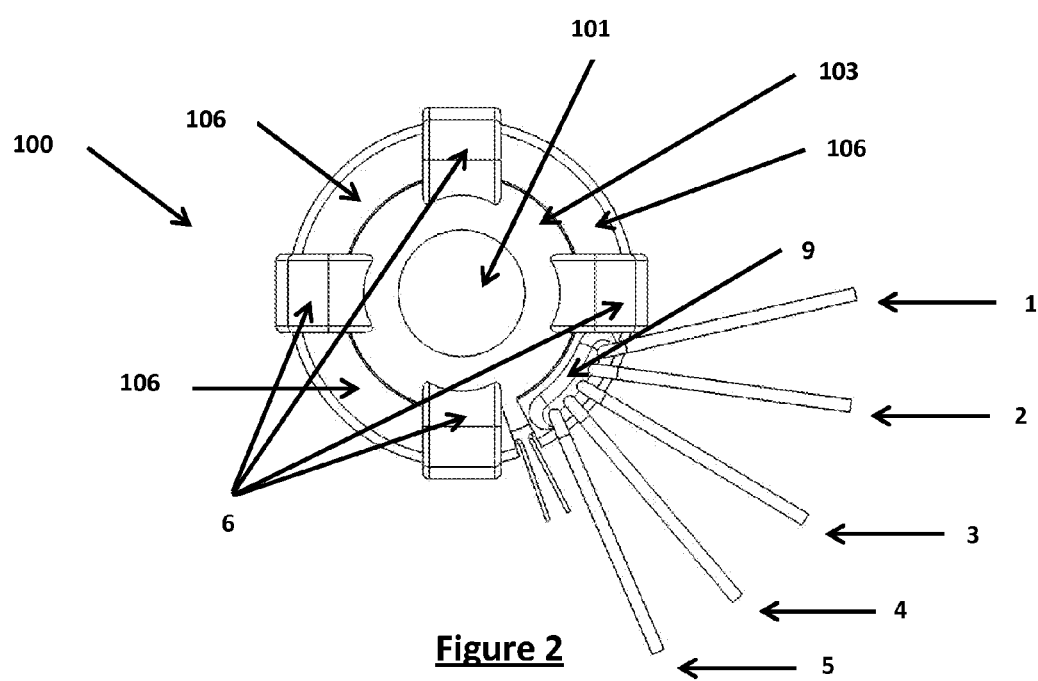
FIG. 2 depicts the top view of an Equatorial Sclera-Mat System placed in the scleral equatorial region beneath the four rectus muscles.
Figure 3:
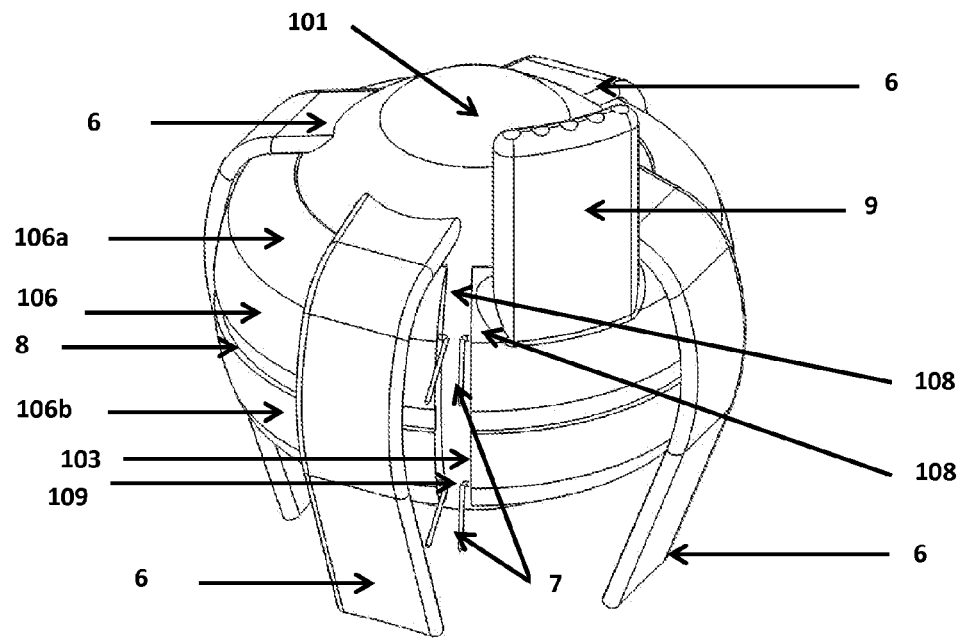
FIG. 3 depicts an in-use perspective of an Equatorial Sclera-Mat System.
Figure 4:
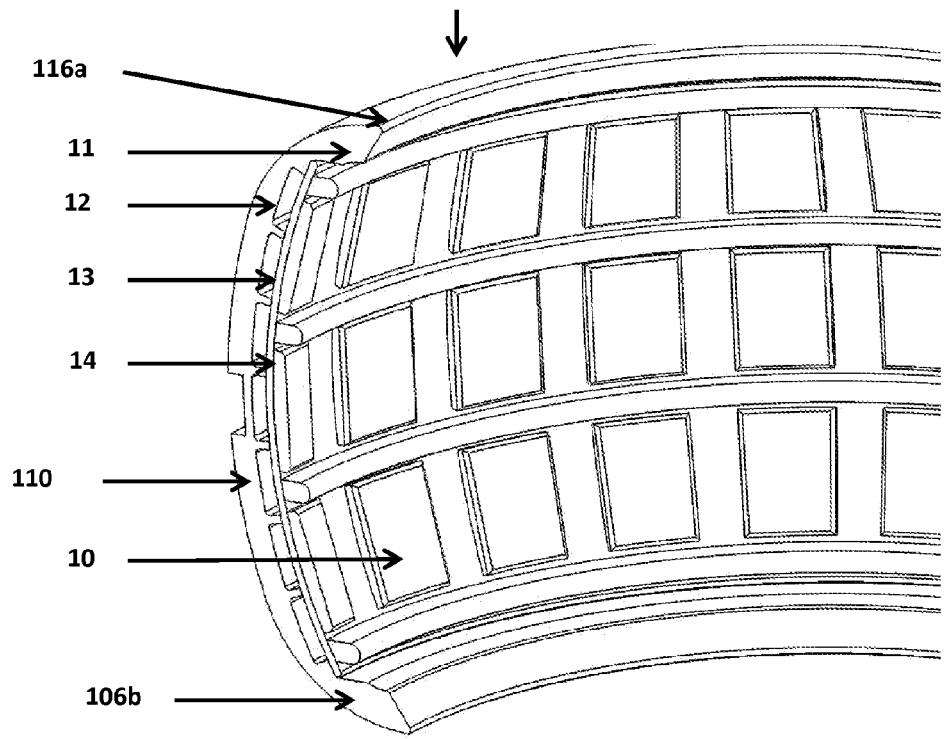
FIG. 4 depicts an inside cut-way view of an Equatorial Sclera-Mat System.

FIGS. 2, 3, 4, and 5 depict an Equatorial Sclera-Mat System. This Equatorial Sclera-Mat System (100) comprises both components for R/F delivery and UVA delivery to scleral tissue. FIG. 2 depicts an in-use top view of an Equatorial Sclera-Mat System (100) placed in the scleral equatorial region (103) (shown in FIG. 3) beneath the four rectus muscles (6). FIG. 3 depicts an in-use perspective of an Equatorial Sclera-Mat following insertion onto the scleral equatorial region (18) of the eye, beneath the rectus muscles (6), and held in place by a band (8). FIG. 4 depicts an inside cut-away view of the components in an Equatorial Sclera-Mat (section 106).

The Equatorial Sclera-Mat System (100) shown in FIGS. 2-5 includes an Equatorial Sclera-Mat (106) which has a cylindrical belt-like configuration. The Equatorial Sclera-Mat (106) has a roughly cylindrically-shaped curvature about a cylindrical axis with an inward curvature or taper along the cylindrical axis in an upper portion (106a) and a lower portion (106b). The circumference of the Equatorial Sclera-Mat (106) has a slit (109) in or through its wall extending along the cylindrical axis or longitudinally along its entire length from the top edge or end of the upper portion (106a) to the bottom end or edge of the lower portion (106b). The Equatorial Sclera-Mat (106) has an outer convex surface (shown in FIG. 3) and an inner concave surface (shown in FIG. 4). The cylindrical curvature and the inward curvature of the upper and lower portions (106a) and (106b) are designed so that the inner concave surface of the Equatorial Sclera-Mat conforms to the equatorial surface of the sclera (103).

As shown in FIG. 2 and FIG. 3 the Equatorial Sclera-Mat (106) is inserted onto the equatorial region of the sclera (103), beneath the conjunctiva (not shown) and under each of the four rectus muscles (6), following a peritomy. FIG. 2 shows a top view of the Equatorial Sclera-Mat (106) disposed around the equatorial region of the sclera (103) so that the inner concave surface of the Equatorial Sclera-Mat 106 conforms to a surface (18) of the sclera (103). As shown in FIG. 3, the respective ends (108) of the Equatorial Sclera-Mat (106) are joined together with sutures (7), sealing the Sclera-Mat and closing slit (109), and held in place with a band (8). Sutures (7) are exemplary and the ends of the Equatorial Sclera-Mat (106) can be joined in other ways.

As shown in FIGS. 2 and 3, the Equatorial Sclera-Mat includes a port 9 which contains the electronic controls and fluidic pathways. Connector tab (9) includes an R/F reservoir (1), a R/F drain (2) a saline coolant reservoir (3), a coolant drain, and (4), electronic controls (5). R/F is pumped into the Equatorial Sclera-Mat from the R/F reservoir (1), and thereupon it comes in contact with scleral surface (18) and is absorbed. Following such absorption of the R/F into the scleral tissue, the R/F is then activated with UVA LEDs (10) [FIG. 4] disposed on the inner concave surface of the Equatorial Sclera-Mat (106). The interface to the UVA LED power supply and the ports which supply and drain the coolant and riboflavin reservoirs are embedded in a connector tab (9) which extends approximately 6 cm. The electronic controls (5) modulate the power supplied to the UVA LEDs and monitor the temperature of saline coolant in the Equatorial Sclera-Mat. Also, the PC displays and controls the R/F soak time and the UVA irradiation exposure time.

FIG. 4 depicts an inner surface and edge (110) of the inner concave surface of the Equatorial Sclera-Mat (106). FIG. 4 shows that the LED's (10) are embedded in the inner concave surface of Equatorial Sclera-Mat (106). Lateral boundary seals (11) are configured to prevent loss of R/F fluid. The Equatorial Sclera-Mat has coolant channels (13) and the coolant channel cover with ribs (12) provides uniform and reliable coolant flow, plus structural stability. The coolant channels enable the flow of saline or some other coolant fluid over the PCB (14) to extract the excess heat generated by the LEDs (10).

A formulation with R/F in a range of concentration from 0.1% to 1.0% is injected into the Equatorial Sclera-Mat from the reservoir (1). The R/F flows through Equatorial Sclera-Mat channels (17) [ ] and soaks the scleral tissue from the scleral surface (18) up to a depth of approximately 1 mm. The duration of the R/F soaking is approximately 5 to 30 minutes. Following this soaking step, the excess R/F on the scleral surface (18) is washed away by circulating saline through the same Equatorial Sclera-Mat channels (17).

The next step includes the application of the UVA irradiance, typically 50 mW/cm2, but which may range from 3 mW/cm2 to 100 mW/cm2, for a period of approximately 3 to 30 minutes. This step uniformly irradiates the equatorial region of the sclera 103 over a circumferential length of approximately 70 mm, and a width of approximately 10 mm. The Equatorial Sclera-Mat has a thickness (Tsm) of 2 mm to 4 mm.

Figure 5:
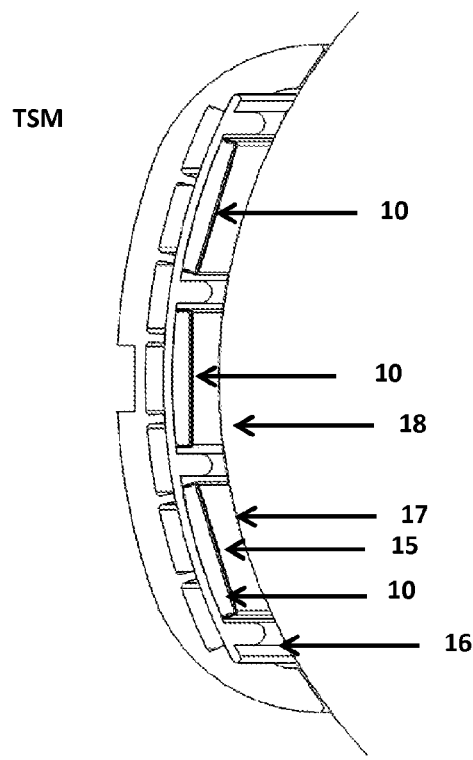
FIG. 5 depicts a cross-sectional view of an Equatorial Sclera-Mat System.

FIG. 5 illustrates a detailed cross-sectional view of the edge (110) of the Equatorial Sclera-Mat (106) and channel support ribs (16). The inner concave surface of the Equatorial Sclera-Mat (106) includes a LED protector (15) that prevents saline or R/F in the channel below (17) from coming in contact with the LEDs (10), R/F is delivered to the surface of the sclera (18) through the channel (17) and excess R/F is washed from the surface of the sclera by the flow of saline through this channel.

Figure 6:
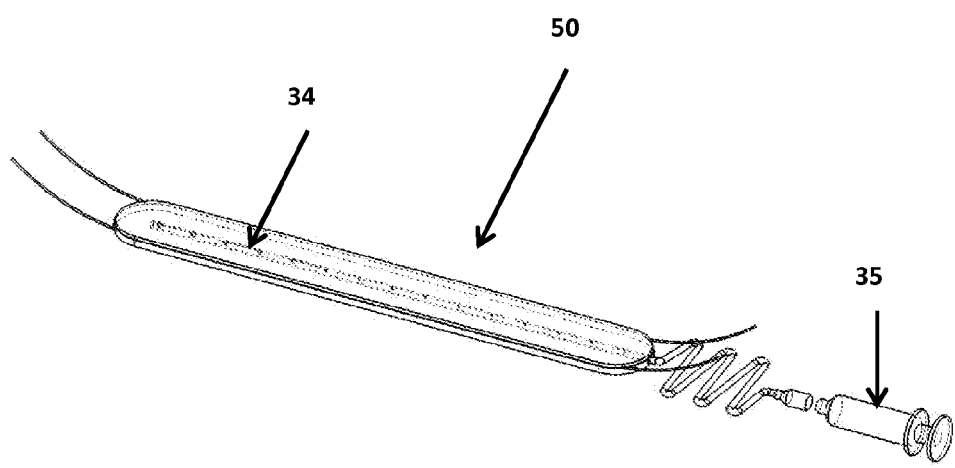
FIG. 6 depicts an equatorial Sponge-Mat for R/F delivery onto the sclera, and which Sponge-Mat contains embedded tubing.

FIG. 6 depicts the top view of a single-sided scleral equatorial Sponge-Mat (50) for R/F delivery with embedded tubing (34), wherein the bottom side is affixed to the sclera surface (18). R/F is injected into this Sponge-Mat with a syringe (35). This type of R/F delivery can be used as an alternative to delivering R/F through the Equatorial Sclera-Mat.

Figure 7:
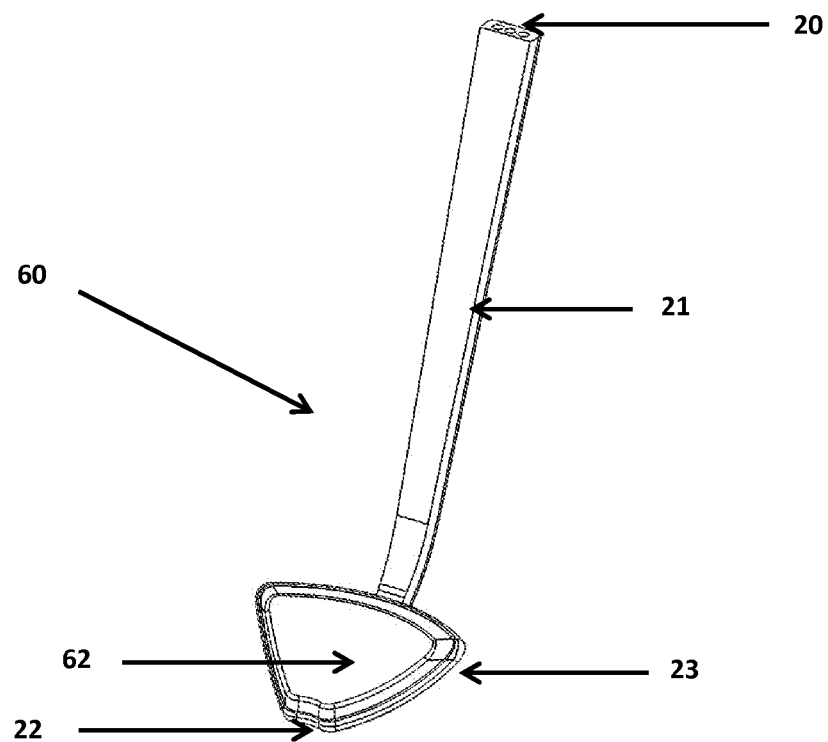
FIG. 7 depicts a posterior Sponge-Mat for R/F delivery to posterior sclera. t

FIG. 7 depicts a posterior Sponge-Mat (60) for R/F delivery to the posterior segment of the sclera. The Sponge-Mat (60) includes a handle (21) attached to an R/F applicator (22) which has a contoured, triangular, concave shaped surface. The applicator is composed of a sponge (62) mounted on a rigid, solid polymer backing (23). The applicator (22) is sized to be inserted at the posterior segment of the sclera (101). The contoured surface of applicator (22) is shaped to be applied against and conform to the surface of the posterior segment of the sclera (101). The handle (21) has a slight outward curvature as it approaches the R/F applicator (22) to facilitate insertion of the R/F applicator (22) into the posterior segment of the sclera (103). R/F is injected into the R/F injection port (20), which is located in the handle (21) of the Sponge-Mat (60). The handle (21) includes a channel (not shown) that connects the port (20) to the applicator (22) and sponge (62). Upon saturation of the contoured sponge, which is placed directly on scleral tissue, the R/F is thereupon absorbed into such tissue. The indented configuration of this R/F applicator (22) is designed to preclude any contact with the optic nerve. The Sponge-Mat 50 is inserted onto the posterior segment of the sclera through the use of a Schepens orbital retractor, which is attached to a hook (not shown) on the handle of Sponge-Mat.

Figure 8:
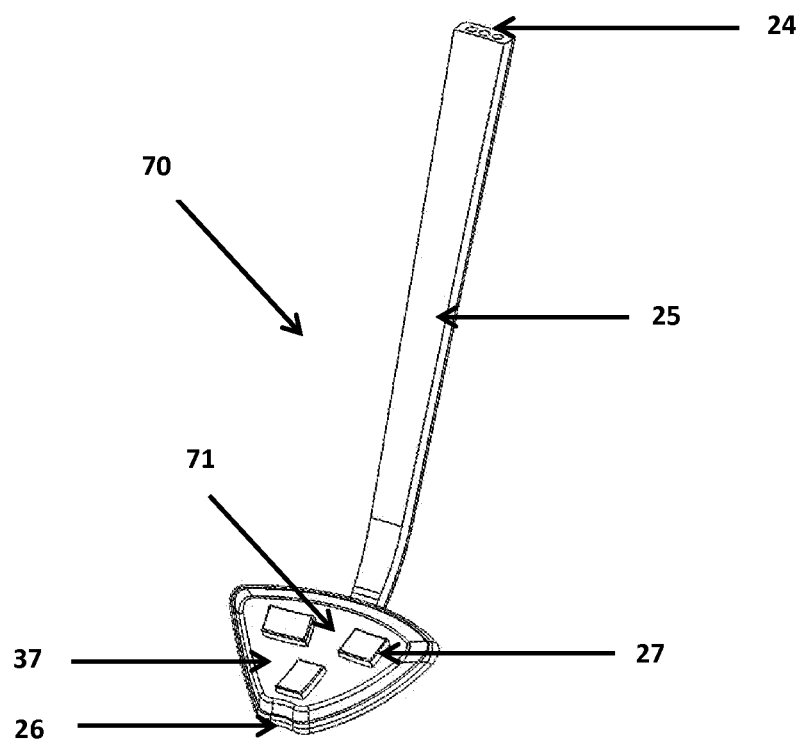
FIG. 8 depicts a posterior UVA-Mat for UVA delivery to posterior sclera.

FIG. 8 depicts a posterior UVA-Mat (70) for UVA delivery to the posterior segment of the sclera 103. The UVA-Mat (70)

includes a handle (25) attached to an UVA applicator (26) which has a contoured, triangular, concave shaped surface (71). The contoured surface of the UVA applicator is configured to be applied against and conform to the surface of the posterior segment of the sclera (101). The handle (25) has a slight outward curvature as it approaches the UVA applicator (26) to facilitate insertion of the UVA applicator (26) into the posterior segment of the sclera (101). The handle (25) includes ports (24), one of which is an electrical port for UVA power supply and two ports for circulating coolant, all of which are embedded in the handle (25). The UVA applicator (26) includes LEDs (27) attached or embedded in the surface (71) of the UVA applicator (26) that provide photosensitizer activation of the R/F. There is a protective cover over the LEDs (27) which creates a barrier between the LEDs and scleral tissue. The LEDs are attached to a PCB (37) which has a coolant channel (not shown) on the top side. Placement of the UVA-Mat (70) is also done with a Schepens orbital retractor.

Figure 9:
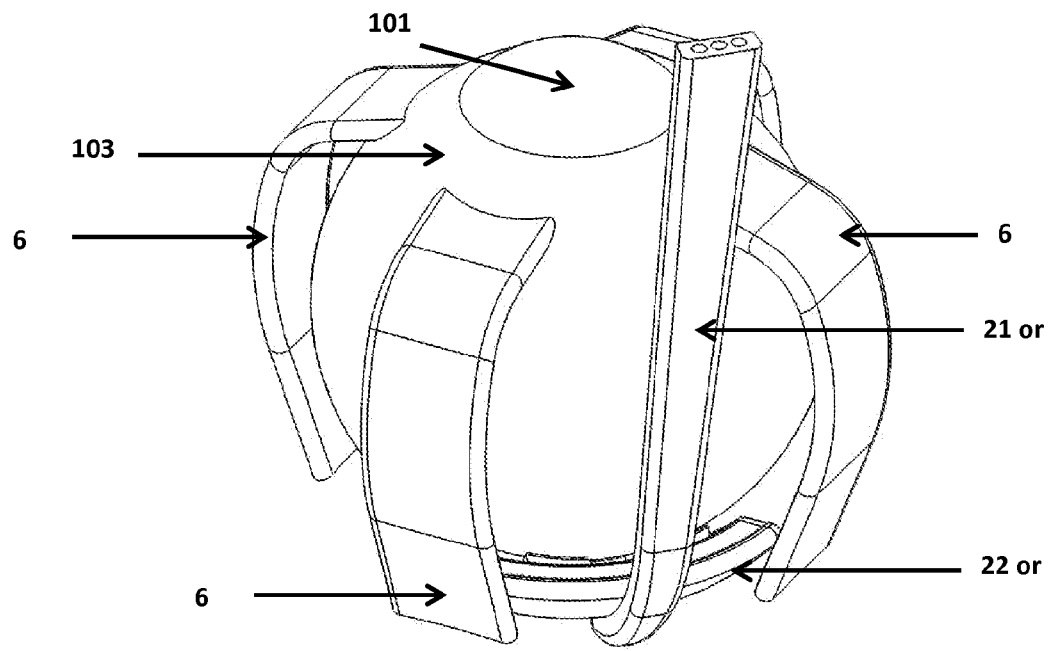
FIG. 9 depicts an in-use application of either the posterior Sponge-Mat or the posterior UVA-Mat

FIG. 9 depicts the in-use application of either one of the posterior Sponge-Mats (60) or one of the UVA-Mats (70), shown between two of the four rectus muscles (6). The handle of either the Sponge-Mat (21) or UVA-Mat (25) is shown projecting outward from the posterior of the sclera between the two rectus muscles (6). The R/F applicator (22) or UVA applicator (26) is disposed at the posterior of the sclera (103) with either of their concave surfaces in contact with the posterior surface of the sclera (101).

FIG. 10 depicts an anterior Sponge-Mat (80) for R/F delivery to the anterior segment of the sclera (103). This Sponge-Mat (80) has an annular or donut shaped portion (30) with an outer circular surface (82), inner circular surface (86), top surface (84), and bottom surface (not shown) with a hole (29) allowing it to conform to the curvature of the anterior sclera. This Sponge-Mat is designed to avoid contact with the cornea when in place on the anterior segment of the sclera (103) with the bottom surface in contact with the sclera surface. The bottom surface has an inward radial curvature or a frusto-conical-like surface to allow the bottom surface to conform to the sclera surface. The donut-shaped portion (30) has an outer diameter (OD) of 16 mm to 22 mm, an inner diameter (ID) of 12 mm to 15 mm, and thickness (T) about 2 to 4 mm. The Sponge-Mat (80) includes an R/F port (28) which is connected to channels embedded in portion (30) that uniformly delivers the R/F fluid to the anterior segment of the sclera (103) when the Sponge-Mat (80) is placed over the anterior segment of sclera (103).

FIG. 11 depicts an anterior UVA-mat (90). This UVA-mat (90) has an annular donut shaped portion (30a) with an outer circular surface (92), an inner circular surface (96), top surface (not shown), and bottom surface (94) with a hole (29a), which avoids contact with the cornea. The bottom surface (94) has an inward radial curvature or frusto-conical-like surface to allow the portion (30a) to conform to the sclera surface. The donut-shaped portion (30) has an outer diameter (OD) of 16 mm to 22 mm, an inner diameter (ID); of 12 mm to 15 mm, and thickness (T) about 2 to 4 mm. The UVA-Mat (90) contains an electrical port (31) and coolant ports (32) extending from the top surface. Similar to the aforementioned designs, this mat also contains LEDs (33) embedded in a PCB (34) at the bottom surface (94) with a coolant system. The range of dimensions of this anterior scleral UVA mat are 16 to 22 mm outer diameter (OD), 12 mm to 15 mm inner diameter (ID) and is about 2 to 4 mm thick (T). The meridional radius of curvature is about 10 to 15 mm. When the UVA-Mat (90) is placed over the anterior portion of the sclera with the bottom surface (94) in contact with the sclera surface, the LEDs deliver UVA into the scleral tissue.

Figure 12:
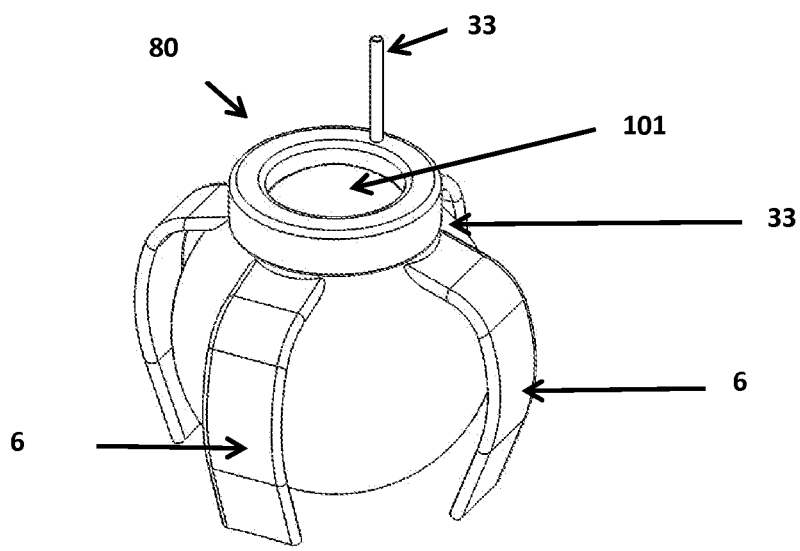
FIG. 12 depicts an in-use application of either the anterior Sponge-Mat or the anterior UVA-Mat

FIG. 12—depicts an in-use anterior sclera Sponge-Mat (80) or an anterior sclera UVA-Mat with a curvature matching the sclera surface (label). Following a full or partial peritomy procedure, the sclera is soaked with an R/F by application of the Sponge-Mat (80) for 5 to 60 minutes. Upon completion of this R/F soaking, the Sponge-Mat (80) is removed and the UVA-Mat (FIG. 10) is placed onto the anterior sclera, symmetrically centered on the cornea. The UVA-Mat LEDs (34) project UVA onto the anterior sclera but not onto the cornea (36). Coolant flow on the back surface of the PCB (34), under which the UVA LEDs are mounted, will ensure thermal safety throughout the exposure. A 5 to 15 minute duration of UVA exposure for sensitizer activation is applied. During this application, coolant circulates through the device. Side-emitting optical fibers are typically fabricated by introducing scattering prismatic defects along an unclad fiber. Those skilled in the art will recognize various ways of accomplishing introducing scattering prismatic defects along an unclad fiber (abrasion, hot stamping, femto-second/excimer laser, prismatic film etc). While many sources for UVA are known in the arts, the use of calibrated, temperature stable fiber delivery devices able to pulsate (over 200 KHz) and fractionate (duty cycle: CW to 1:10 range for example) with high intensity (over 100 mW at 365 nm, such as the Omicron LEDMOD-365) are useful in these embodiments.

The embodiments as illustrated in FIGS. 2-12) may be used to deliver a sclera scaffolding material (such as recombinant human collagen) that may enable cross-linked (using riboflavin) to occur in situ on the sclera. Such a process would create a structure on the sclera that would augment cellular regrowth within the scleral tissue. These embodiments also facilitate the introduction of oxygen gas and oxygen enhancers, such as deuterated water or perfluorinated oxygen carriers (commercially known as Oxygent and Oxycyte), to increase the efficiency of cross-linking. Besides the photosensitizer riboflavin, other types, such as rose bengal, methylene blue, indo cyanine green, etc. can be dispensed/delivered with the embodiments set forth herein. Additionally, chemical cross-linking agents can be used in the embodiments mentioned herein, and these may include, without limitation: genipin, threose, methylglyoxal, glyceraldehyde, aliphatic β-nitro alcohols, etc and nutraceuticals such as black currant extract.

What we claim:

1. A method of treating progressive myopia comprising:
providing an apparatus that upon insertion will deliver a drug formulation comprising riboflavin to scleral ocular tissue of a sclera of an eye of a patient in need of treatment for progressive myopia;
inserting the apparatus through an opening in a conjunctiva to deliver to deliver the drug formulation to targeted regions of the scleral ocular tissue; and
allowing the drug formulation to diffuse from the apparatus into the targeted regions of the scleral tissue to soak the scleral tissue,
wherein the apparatus is disposed in and delivers the drug formulation to an equatorial region of the sclera beneath the rectus muscles and the four quadrants of the sclera between the rectus muscles,
wherein the drug formulation comprises riboflavin capable of being activated by UVA radiation for purposes of inducing cross-linking of scleral collagen tissue, and
wherein the crosslinking imparts and increase in biomechanical rigidity or stiffness to the treated ocular tissue to reduce, limit, and/or arrest elongation of the eye that is characteristic of the progressive myopia.

2. The method of claim 1, wherein the apparatus is disposed in and delivers the drug formulation to an anterior segment of the sclera.

3. The method of claim 1, wherein the apparatus is disposed in and delivers the drug formulation to a posterior segment of the sclera.

4. The method of claim 1, wherein the apparatus contains channels for delivering the drug formulation onto a surface of the sclera, and thereby enabling the riboflavin to soak into collagen tissue of the sclera.

5. The method of claim 1, wherein the apparatus includes a system to rinse excess drug formulation from the scleral surface after soaking.

6. The method of claim 1, further comprising delivering UVA radiation to the targeted regions of the scleral tissue which cross-links scleral collagen tissue exposed to the delivered formulation which imparts the increase in biomechanical rigidity or stiffness to the treated ocular tissue which reduces, limits, and/or arrests elongation of the eye that is characteristic of the progressive myopia.

* * * * *